United States Patent [19]
Beden et al.

[11] Patent Number: 5,871,694
[45] Date of Patent: Feb. 16, 1999

[54] DEVICE FOR PROVIDING A SUBSTITUATE

[75] Inventors: Josef Beden, Mainz-Kastel; Hans-Jurgen Flaig, Lauterbach; Bernd Steinbach, Friedberg, all of Germany

[73] Assignee: Fresenius AG, Germany

[21] Appl. No.: 762,472

[22] Filed: Dec. 9, 1996

[30] Foreign Application Priority Data

Dec. 9, 1995 [DE] Germany ............ 195 46 027.8

[51] Int. Cl.$^6$ ............ A61M 1/14; B01D 63/00
[52] U.S. Cl. ............ 422/44; 210/101; 210/321.71; 210/321.72; 210/646; 210/929; 604/5
[58] Field of Search ............ 422/44; 210/257.2, 210/258, 416.1, 767, 101, 321.65, 321.71, 321.72, 929, 645, 646; 604/5

[56] References Cited

U.S. PATENT DOCUMENTS 4,267,040  5/1981  Schäl .

FOREIGN PATENT DOCUMENTS

| 0 001 074 | 3/1979 | European Pat. Off. . |
| 0 226 720 | 7/1987 | European Pat. Off. . |
| 0 321 754 | 6/1989 | European Pat. Off. . |
| 41 16 178 | 11/1992 | Germany . |
| 39 18 078 | 8/1993 | Germany . |

*Primary Examiner*—E. Leigh McKane
*Attorney, Agent, or Firm*—Kenyon & Kenyon

[57] ABSTRACT

In a device for providing a substituate to a device for removing toxic substances from the blood which employs volumetric balancing of the fluid, an equalization chamber (11, 20) communicates with first and second inlet lines (9, 18) respectively, of a balancing chamber (14). Moreover, a buffer chamber (23) communicates with the first and/or second outlet line (15, 22) of the balancing chamber (14). The volume prevailing in the buffer chamber (23) that communicates with the first or second outlet line (15 or 22) can be so varied that the volume expands when the second or first equalization chamber (20 or 11) is emptied, and is reduced when the second or first equalization chamber is filled. As a result, the discontinuous pulse is smoothed on the outlet side of the balancing chamber.

8 Claims, 4 Drawing Sheets

DEVICE FOR PROVIDING A SUBSTITUATE

BACKGROUND OF THE INVENTION

1. Field of the Invention

The invention relates generally to a device for removing toxic substances from the blood.

2. Description of Related Art

When faced with chronic renal failure, different blood-purification or blood-treatment methods are applied, in which apparatuses are employed to remove those substances which are usually eliminated with the urine, and to withdraw fluids. The predominant method used in hemodialysis (HD) is the diffusive transfer of substances; in hemofiltration (HF), it is the convective transfer of substances across a membrane. A combination of the two methods is called hemodiafiltration (HDF). In peritoneal dialysis (PD), no extracorporeal circuit is needed, and the peritoneum is used as the contact membrane.

Because of the large exchange volumes entailed in the named methods, as well as in continuous arteriovenous HF, continuous veno-venous HF, and in plasma-filtration (PF), there must be a precise balancing of the withdrawn fluid, on the one hand, and of the supplied fluid, on the other hand, and of the volume to be ultrafiltrated over the entire treatment time. Gravimetric and volumetric balancing systems are known from the related art.

German Patent 41 16 178 C1 describes a device for purifying blood, in which a volumetric fluid balancing is performed for HF, HDF, and PF systems. The known hemotherapeutic device has a balancing chamber, which is partitioned by a flexible wall into a first and a second balancing-chamber half, the first chamber half communicating with a filtrate line, and the second chamber half with a substituate line. A filtrate outlet line branches off from the first chamber half to an outlet, while a substituate line, which communicates with the circulatory system, branches off from the second chamber half. The filtrate and the substituate are alternately supplied, as the case may be, to the balancing chamber from an equalization chamber which communicates with the filtrate or substituate line by means of a pressure device. When working with the known filtration device, the equalization chambers are filled by a filtrate pump or a substituate pump and, after the cut-off clamps are opened, are emptied by means of the pressure device into one of the balancing chamber halves. The cutoff clamps are inserted in such a way that when the filtrate flows in, the substituate flows out, whereas when the substituate flows in the filtrate flows out. Accordingly, two pairs of clamps are alternately switched over into the other respective operating position. The drawback is that when only one balancing volume is used, a discontinuous flow occurs, which leads to pulsation.

When the disposable balancing unit is used in PD, the principle applies accordingly. In this case, however, substituate is not continuously balanced with the filtrate, but rather, using additional clamps and connections, fresh dialysate is first supplied via both balancing chamber halves and, after being retained in the abdominal cavity, the consumed dialysate is conveyed in the same manner into the outflow, i.e., there is no direct displacement of substituate through the filtrate, and vice versa. The volumes [quantities] are balanced by adding the individual volumes which are carried away [removed] or supplied per chamber filling.

German Patent 39 18 078 C2 describes a device for single-needle dialysis, in which a stream of untreated blood flows from the patient to the arterial line during an arterial suction phase, and a stream of treated blood flows back to the patient through the venous line during a venous return phase. It is proposed that an expansion chamber be provided upstream and downstream from the dialyzer and that the device for the single-needle dialysis be operated in four consecutive phases, namely the suction phase, a first transition phase, the return phase and a second transition phase. The chambers arranged upstream and downstream from the dialyzer are simultaneously filled during the suction phase and simultaneously emptied during the return phase.

SUMMARY OF THE INVENTION

It is an object of the invention to create a device for removing toxic substances from the blood by means of volumetric fluid balancing, during which the occurrence of a pulsating flow would be largely avoided.

With the device according to the invention for removing toxic substances from the blood, a buffer chamber of variable volume is connected to the first and/or second outlet line. In the case where the buffer chamber is connected to the first outlet line, the added volume is always exactly provided when the second equalization chamber is emptied into the second balancing chamber half as the fluid from the first balancing chamber half is displaced. This enables the buffer chamber to fill with fluid. When, on the contrary, however, the fluid flows into the second equalization chamber, the volume of the buffer chamber is reduced, so that the fluid it contains slowly flows out and the discontinuous pulse can be smoothed. In the case where the buffer chamber is connected to the second outlet line, the added volume is always made available then exactly when the first equalization chamber is emptied into the first balancing chamber half with displacement of the fluid from the second balancing chamber half. However, to smooth the discontinuous pulse, a buffer chamber can also be provided in either outlet line of the balancing chamber.

In principle, it is possible for the volume of the buffer chamber to be made available even immediately before the first or second equalization chamber is emptied. However, it is advantageous to gradually expand the volume of the buffer chamber when the first or second equalization chamber is emptied. In the event that the maximum volume of the buffer chamber is smaller than the volume of the corresponding equalization chamber, or the volume of the buffer chamber is expanded more slowly than the volume of the equalization chamber decreases, it can be ensured that fluid will always flow into the outlet line during the filling operation of the buffer chamber as well.

It is expedient for the first and second equalization chambers to be pressurized by means of compression devices so that they empty autonomously into the corresponding balancing chamber half when the clamping arrangements are opened.

In a preferred embodiment, the compression arrangement of the first and second equalization chamber has, in each case, two pressure elements which are compressed by a spring element and extend above and below the chamber. Also provided are two pressure elements which overlap and underlap the buffer chamber, the pressure elements of the buffer chamber that is connected to the first or second outlet line, respectively, and of the second or first equalization chamber, respectively, being so coupled that they execute an oppositely directed movement. As a result, the volume of the buffer chamber expands when the corresponding equalization chamber is emptied and is reduced when the corresponding equalization chamber is filled.

In an especially simple and trouble-free specific embodiment, the pressure elements are coupled mechanically by means of a rocker. For this purpose, one of the two pressure elements of the equalization chamber or buffer chamber is permanently mounted, while the other of the two pressure elements is movably guided. The movably guided pressure elements are coupled by way of a connecting element, which is swivel-mounted between its ends. By varying the lever ratio, the extent that the volume prevailing in the buffer chamber changes can be adjusted to achieve optimal smoothing.

Since the total amount of fluid in a given cycle is conveyed all at once due to the temporary storage in the buffer chamber, the counterpressure being thereby reduced and the pressure being automatically transferred to the respective equalization chamber by means of the coupling, the required spring resistance of the compression device of the corresponding equalization chamber can be reduced.

A more detailed explanation of an exemplary embodiment according to the invention follows with reference to the drawings.

DETAILED DESCRIPTION OF THE INVENTION

Figure 1:
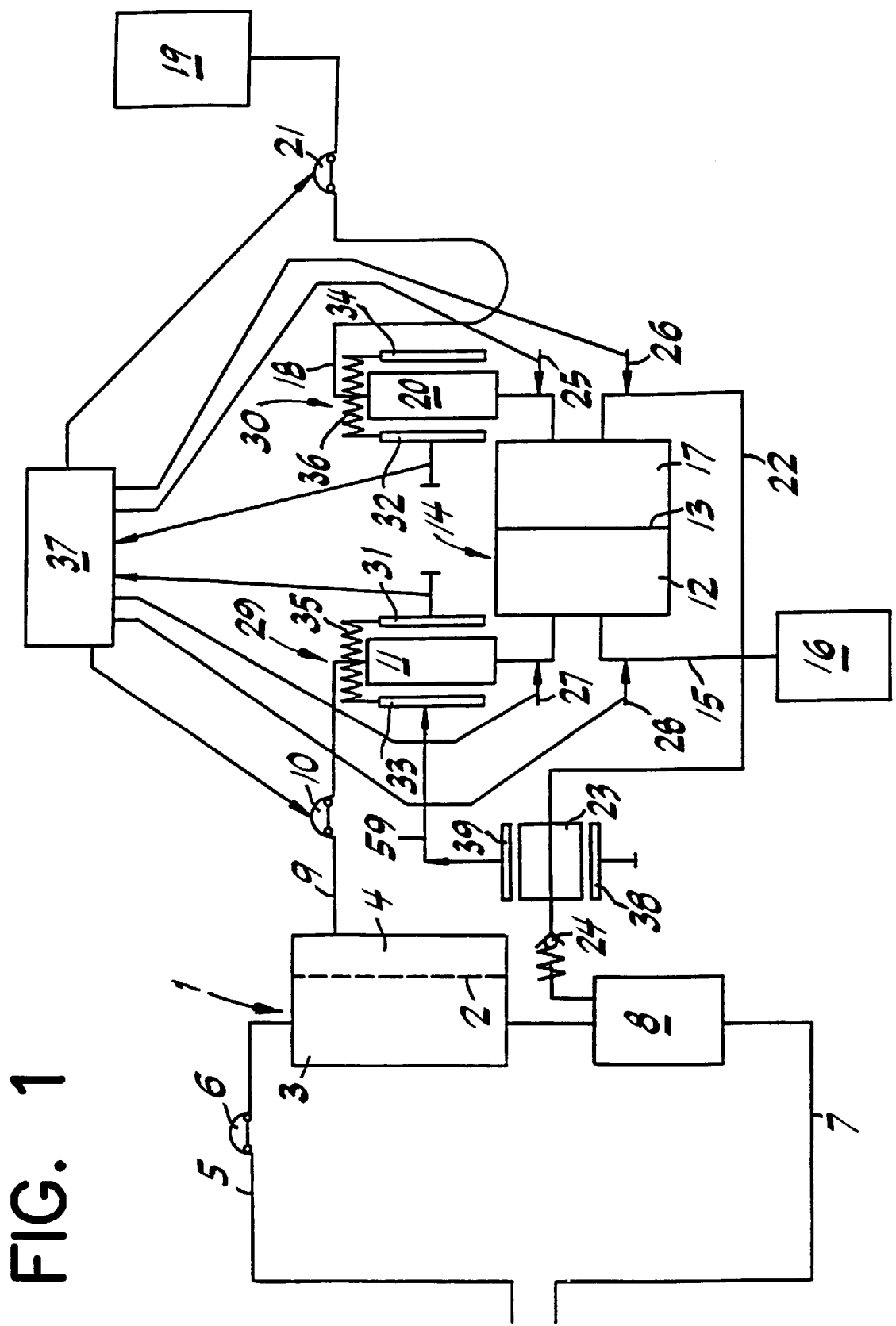
FIG. 1 is a schematic representation of a blood purification device with a filtrate/substituate balancing arrangement.

FIG. 1 illustrates a form of embodiment of the device for removing toxic substances from the blood in which the balancing arrangement according to the invention can be advantageously used. The basic principle of the filtration arrangement is known from German patent 41 16 178 C1, the disclosure of which is incorporated herein by reference. The filtration arrangement has a filter 1 which is divided by a semipermeable membrane 2 into a blood chamber 3 and a filtrate chamber 4. The inlet of the chamber 3 communicates with a blood feed line 5 which leads to the patient and has a blood pump 6 connected thereto. A drip chamber 8 communicates with blood outflow line 7 leading to the patient.

On the filtrate side, filtrate chamber 4 is connected via a first inlet line 9, which has a first pump 10 and a first equalization chamber 11 connected thereto, to the inlet of first balancing chamber half 12 of a balancing chamber 14 that is divided into two balancing chamber halves by a flexible wall 13. A first outlet line 15 runs from the outlet of first balancing chamber half 12 to drain 16.

The inlet of second balancing chamber half 17 communicates via a second inlet line 18 with a substituate source 19. A second equalization chamber 20 and a second pump 21 are connected to second inlet line 18. A second outlet line 22 runs from the outlet of second balancing chamber half 17 to venous drip chamber 8. A buffer chamber 23 is connected to second outlet line 22. A check valve 24 is provided downstream from buffer chamber 23 in second outlet line 22.

First inlet line 9 and first outlet line 15, as well as second inlet line 18 and second outlet line 22 are able to be clamped off by means of clamping arrangements 25 to 28. Balancing chamber 14, first equalization chamber 11, second equalization chamber 20, and buffer chamber 23 are designed as flexible plastic bags and are components of a sheet-type disposable unit, which will described in detail later on with reference to FIGS. 2 and 3.

First equalization chamber 11 and second equalization chamber 20 are each provided with a compression arrangement 29, 30, consisting in each case of a fixed pressure plate 31, 32 and of a movably guided pressure plate 33, 34, which are compressed by way of a spring element 35 or 36. Pressure plate pairs 31, 33 or 32, 34 overlap and underlap equalization chambers 11, 20 and cause them to be emptied into balancing chamber halves 12, 17 by way of lines 9, 18 during the emptying step.

First pump 10 and second pump 21 as well as clamp arrangements 25 to 28 are connected via control lines to a control and regulating unit 37. Moreover, two pressure plates 38, 39 engage with buffer chamber 23, one pressure plate 38 being fixed and the other pressure plate 39 being movably guided. The movably guided pressure plate 39 of buffer chamber 23 is connected to the movably guided pressure plate 33 of first equalization chamber 11 by way of a mechanical coupling still to be described with reference to FIGS. 4 and 5. Pressure plates 33, 39 are so coupled that they move in opposite directions.

Figure 2:
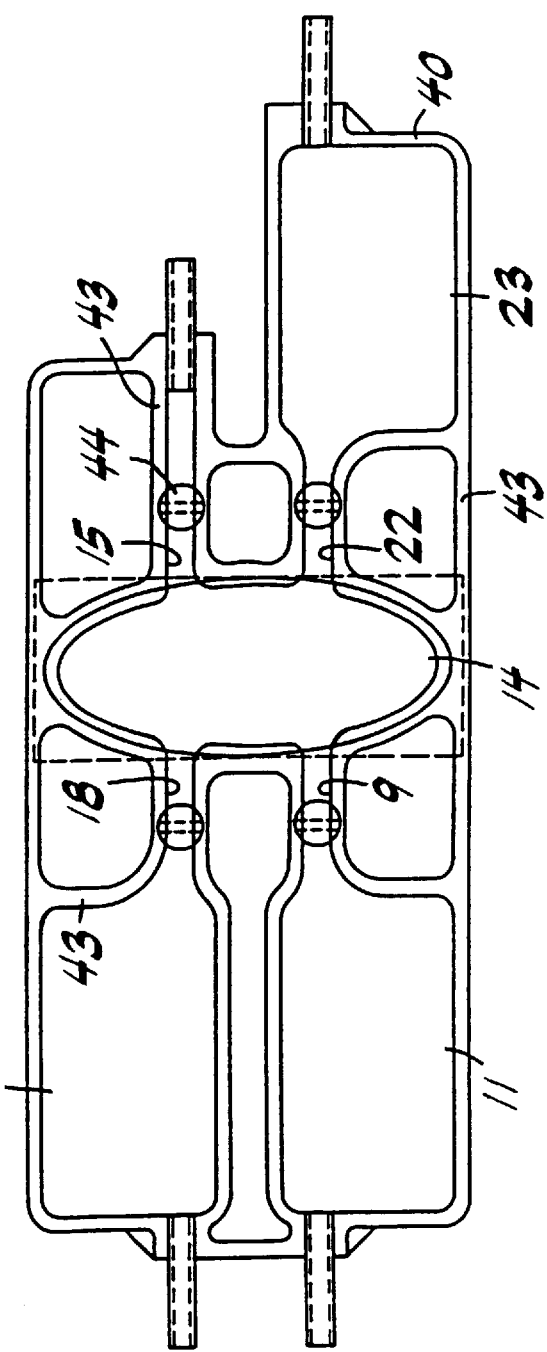
FIG. 2 is a top view of a disposable unit with a balancing chamber, a first equalization chamber, a second equalization chamber, and a buffer chamber.

FIG. 2 shows a top view of the balancing sheet-type disposable unit, comprising balancing chamber 14, first equalization chamber 11, second equalization chamber 20, and buffer chamber 23. The sheet-type disposable unit has two flexible, essentially rectangular plastic sheets 40, 41, which are heat-sealed along the seams identified by reference numeral 43 so as to form four chambers between the upper and lower sheets 40, 41. Located in the center is the oval-shaped balancing chamber 14, first equalization chamber 11 and second equalization chamber 20 being arranged on one side of balancing chamber 14, and buffer chamber 23 on the other side. Fluid-filled chambers 11, 20, 23 have approximately the same volume.

Flexible wall 13, which divides balancing chamber 14 into first and second balancing chamber halves 12, 17, is formed by a rectangular intermediate sheet, as indicated by dashed lines in FIG. 2, that is inserted in the area of the balancing volume between the upper and lower sheets 40, 41 and is heat-sealed to outer sheets 40, 41, forming two chamber halves 12, 17.

First inlet line 9, first outlet line 15, second inlet line 18, and second outlet line 22 are formed within the area of the balancing sheet-type disposable unit as sheet channels, in which plastic hoses not shown in FIG. 2 are embedded and are heat-sealed to upper and lower sheets 40, 41. Not only do the embedded plastic hoses prevent the hose channels from collapsing, but they also create clamping spots 44 that can be pressure-sealed by means of clamping arrangements 25 to 28.

Figure 3:
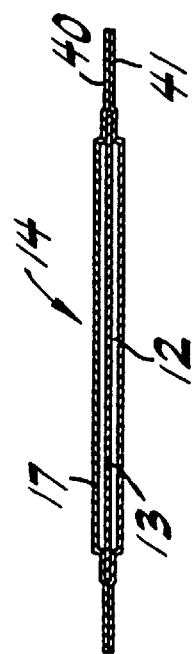
FIG. 3 is a section through the balancing chamber of the disposal unit in FIG. 2.

FIG. 3 illustrates a section through balancing chamber 14 of the unfilled balancing disposable unit. Intermediate sheet 13 is heat-sealed by its outer edge of to the edges of upper and lower sheets 40, 41 and is able to move freely within the balancing chamber between the outer sheets. Because the flexibility of the plastic sheets makes it impossible to observe a constant volume, the balancing volume is defined by a rigid outer form. Therefore, the balancing disposal unit is inserted into a system insert unit which makes up part of the blood purification device.

Figure 4:
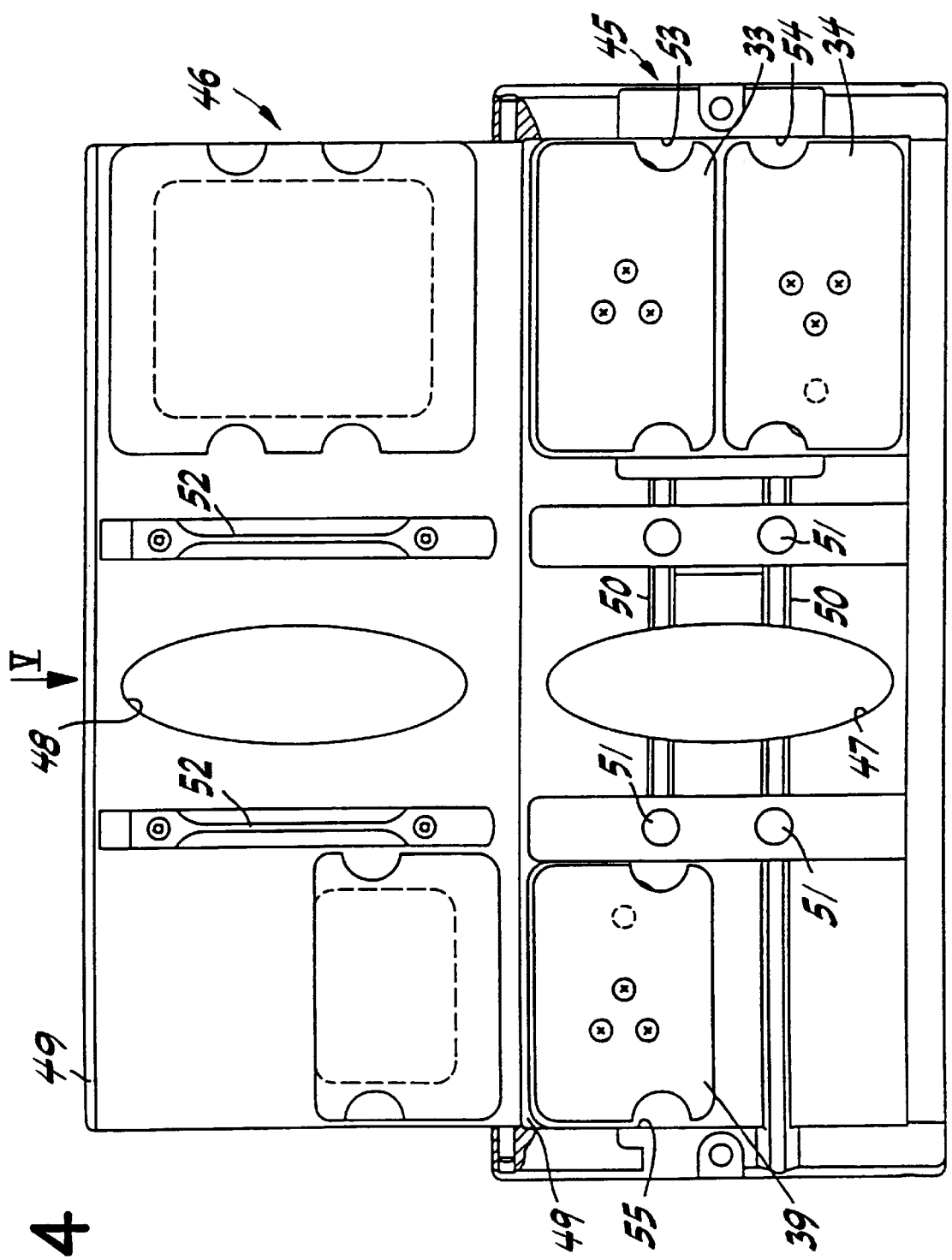
FIG. 4 is a top view of the system insert unit of the blood purification device for receiving the disposable unit.

FIG. 4 is a top view of the unfolded system insert unit, in which the balancing disposable unit can be fittingly inserted. The system insert unit has two receiving bodies 45, 46, each with a recess 47 or 48, respectively, provided in the area of the balancing volume. Recesses 47, 48 of the two receiving bodies 45, 46 are arranged at the center of the two receiving bodies. The upper and lower receiving bodies 45, 46 of the system insert unit are provided with a longitudinal clamping edge 49 which fixes the edge areas of the disposable unit. When the volume between upper sheet 40 and intermediate sheet 13 of balancing chamber 14 is filled with fluid, the other volume between intermediate sheet 13 and lower sheet 41 is emptied by opening and closing the inlets and outlets of chamber 14, respectively, in that intermediate sheet 13 is folded over as a result of displacement. In order for upper and lower sheets 40, 41 of the disposable unit to be able to place themselves tightly against the shell shapes of receiving bodies 45, 46, vents are provided in the receiving bodies. Two parallel guide channels 50 for receiving the inlet and outlet channels are provided in lower receiving body 45 on both sides of recesses 47, 48. Moreover, arranged inside the guide channels are four tappets 51 which cooperate with clamping edges 52 located at the level of the tappets in upper receiving body 46. Clamping spots 44 of the channels of the disposable unit can be clamped off in a pressure tight manner by the electromagnetically actuated tappets 51. Provided laterally next to tappets 51 or clamping edges 52 in lower and upper receiving bodies 45, 46, respectively, are inserts 53, 54, 55 for first and second equalization chambers 11, 20, as well as for buffer chamber 23. Arranged at the bottom of inserts 53, 54 are movably guided and spring-prestressed pressure plates 33, 34, by means of which equalization chambers 11, 20 of the disposable unit are continually pressurized.

The pressure plate at the base of insert 55 of buffer chamber 23 is so mechanically coupled to pressure plate 33 of first equalization chamber 11 that the latter moves in the opposite direction, i.e., when the movably guided pressure plate 33 of first equalization chamber 11 is raised, the movably guided pressure plate 39 of buffer chamber 23 is lowered, and vice versa.

Figure 5:
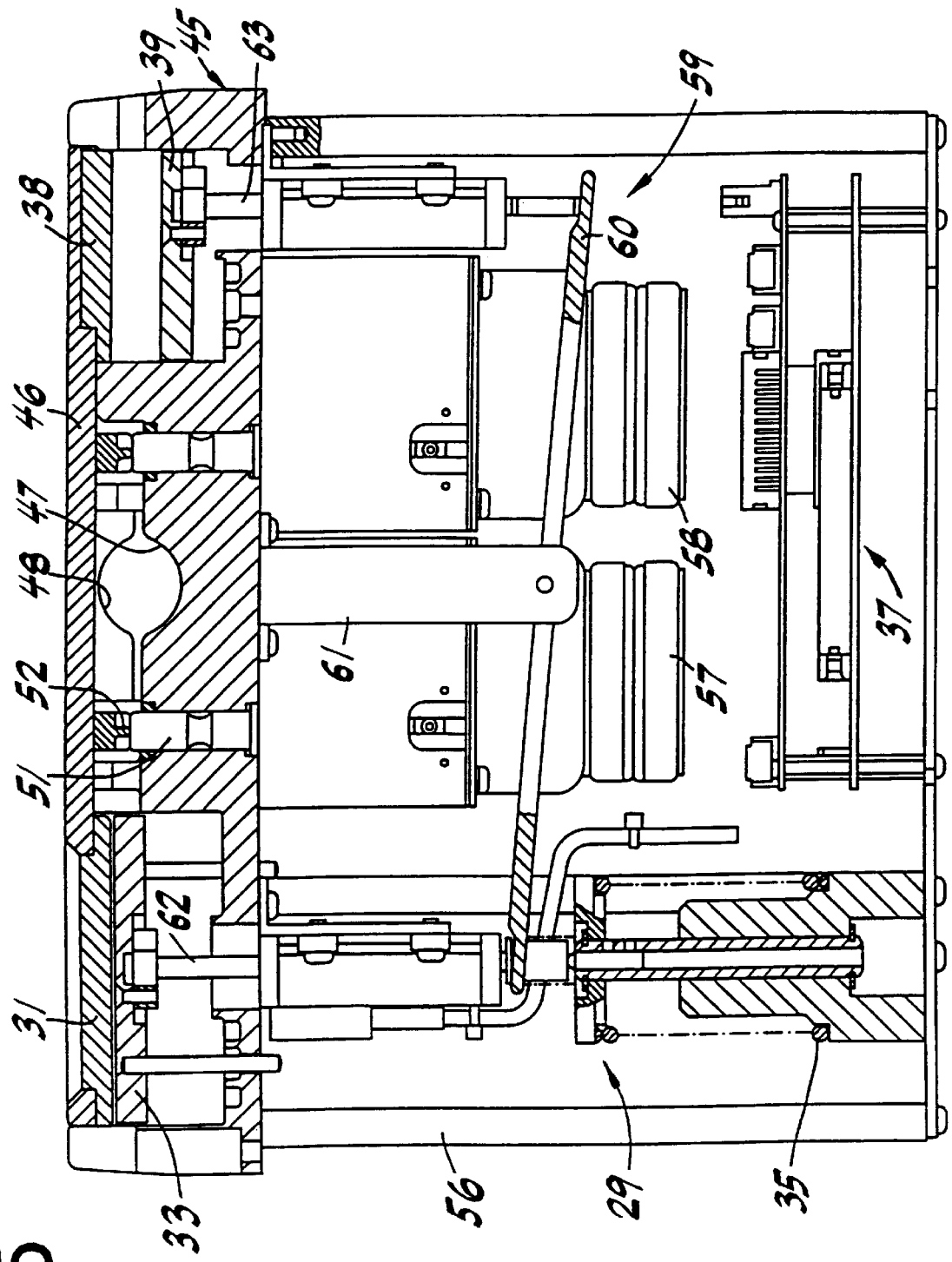
FIG. 5 is a view of the system insert unit along the direction of arrow V of FIG. 4.

FIG. 5 is a side view of the system insert unit. Lower receiving body 45 is supported by a frame 56, which accommodates driving elements 57, 58 for tappets 52, compression arrangements 29, 30 comprising the two pressure plates prestressed by the compression springs, and a board for control and regulating unit 37. Movably guided pressure plate 33 of first equalization chamber 11 and movably guided pressure plate 39 of buffer chamber 23 are mechanically coupled by way of rocker 59. The latter has a connecting element 60, which is swivel-mounted in the middle on a supporting element 61 between its two ends and engages with its ends on guide rods 62, 63 of pressure plates 33, 39. When first equalization chamber 11 is filled and pressure plate 33 is pressed downward counter to the force of pressure spring 35, pressure plate 39 of buffer chamber 23 is raised. On the other hand, lowering pressure plate 39 of buffer chamber 23 causes pressure plate 33 of first equalization chamber 11 to be raised.

The following will elucidate the functional sequence of the balancing process. First equalization chamber 11 is initially filled by means of first pump 10. After clamping arrangement 27 in first inlet line 9 is opened, the flexible, first equalization chamber 11 empties under the pressure of pressure plate 33 into first balancing chamber half 12. The fluid flowing in displaces the fluid contained in second balancing chamber half 17. As first equalization chamber 11 empties, the volume of buffer chamber 23 expands as a result of the lowering of pressure plate 39 to the extent that the volume of first equalization chamber 11 is reduced by the raising of pressure plate 33. The fluid emerging from second balancing chamber half 17 partly fills buffer chamber 23 and then flows off. After the balancing volume is completely filled, first equalization chamber 11 begins to fill again, and second equalization chamber 20 empties while displacing the fluid into the balancing volume. As first equalization chamber 11 fills, the movably guided pressure plate 33 is lowered. The mechanical coupling by way of rocker 59 causes the movably guided pressure plate 39 of buffer chamber 23 to be simultaneously raised, so that the residual fluid contained in the added volume is pressed out. As a result, even when first equalization chamber 11 is filled, the flow is maintained until new fluid is replenished from the balancing volume in the next cycle. The pressure required for this is supplied by the expansion of first equalization chamber 11. The discontinuous pulse is smoothed in this manner.

With reference to the form of embodiment of a device for removing toxic substances from the blood described in FIG. 1, check valve 24 in second outlet line 22 downstream from buffer chamber 23 prevents a distinct pressure drop during dehydration cycles. As soon as the first equalization chamber is emptied, namely, it releases the additional buffer volume by way of the coupling. However, in a dehydration cycle, this volume is not taken up by the substituate, but is filled with air or blood because of the venous counterpressure from drip chamber 8, the pressure prevailing in drip chamber 8 falling in this case. This pressure drop is prevented at the right moment by check valve 24. Alternatively, however, a cutoff valve can also be provided which, when necessary, closes the line to the extracorporeal circuit.

It should also be noted in the above described specific embodiment that the spring resistance of compression arrangement 30 of second equalization chamber 20 must not be rated to be greater than the spring resistance of compression arrangement 29 of first equalization chamber 11, so that balancing chamber 14 can be properly emptied during dehydration cycles, i.e., during cycles when filtration takes place without replacement.

The balancing arrangement comprising a balancing chamber, clamping arrangements, inlet and outlet lines, and at least one buffer chamber, as well as a control unit can also be used advantageously in a peritoneal dialysis device, which enables the peritoneal dialyzing fluid to be cyclically supplied to or withdrawn from a patient in a precisely balanced manner. For this purpose, two inlet lines 9, 18 are united to form one common inlet line, and two outlet lines 15, 22 to form one common outlet line, the dialyzing fluid being alternately directed via the common inlet line into first and second balancing chamber halves 12, 17, and via the common outlet line to the patient's peritoneal cavity. In a peritoneal dialyzer of this type, one buffer chamber advantageously communicates with the first outlet line, and one buffer chamber with the second outlet line. Alternatively, however, one buffer chamber can also be connected into the shared outlet line, following the junction point [point where the two lines are united].

What is claimed is:

1. A device for providing a substituate to a device for removing toxic substances from the blood, comprising:
    a balancing chamber (14), which is divided by a flexible partition (13) into a first balancing chamber half (12) connected to a first inlet line (9) and a second balancing chamber half (17) connected to a second inlet line (18), a first outlet line (15) branching off from the first balancing chamber half (12) and a second outlet line (22) branching off from the second balancing chamber half (17);

clamping arrangements (25 to 28) for shutting off the inlet lines (9, 18) and the outlet lines (15, 22);

a control unit (37) for activating clamping arrangements (25 to 28);

a first equalization chamber (11) connected to the first inlet line (9) and a second equalization chamber (20) connected to the second inlet line (18); and a buffer chamber (23) having a variable volume and fluidly connected to at least one of the first outlet line (15) and the second outlet line (22) of the balancing chamber (14), and a coupling means in communication between the buffer chamber and the first or second equalization chamber, such that the volume of the buffer chamber connected to at least one of the first or second outlet lines is varied, depending on the volume of the first or second equalization chamber (20 or 11), whereby the volume of the buffer chamber expands when the first or second equalization chamber is emptied, and the volume is reduced when that the first or second equalization chamber is filled.

2. The device as defined by claim 1, further comprising two compression arrangements (29,30) positioned to exert pressure on said first and second equalization chambers (11, 20), respectively.

3. The device as defined by claim 2, further comprising a check valve (24) or a cutoff valve provided in said first or second outlet line (15, 22), downstream from said buffer chamber (23).

4. The device as defined by claim 2, wherein said compression arrangements (29, 30) of said first and second equalization chambers (11, 20) each have two pressure elements (31, 33; 32, 34) compressed by a spring element (35, 36) and which overlap and underlap each chamber, and further comprising two pressure elements (38, 39) which respectively underlap and overlap said buffer chamber (23), wherein said coupling means couples the pressure elements (38, 39) of the buffer chamber to said pressure elements (31, 33) of said first or second equalization chamber (20 or 11) such that said pressure elements of said buffer chamber and either of said first and second equalization chambers move in opposite directions.

5. The device as defined by claim 4, further comprising a check valve (24) or a cutoff valve provided in said first or second outlet line (15, 22), downstream from said buffer chamber (23).

6. The device as defined by claim 4, wherein, one of said two pressure elements of said first and second equalization chambers (11, 20) and of said buffer chamber (23), respectively, is fixed and the other of said two pressure elements is movably guided, said coupling means being a connecting element (60) that is swivel-mounted between its ends, and said movably guided pressure element of said buffer chamber (23) and said movably guided pressure element of said first or second equalization chamber (11, 20) are mechanically coupled to one another by way of said connecting element (60).

7. The device as defined by claim 6, further comprising a check valve (24) or a cutoff valve provided in said first or second outlet line (15, 22), downstream from said buffer chamber (23).

8. The device as defined by claim 1, further comprising a check valve (24) or a cutoff valve provided in said first or second outlet line (15, 22), downstream from said buffer chamber (23).

* * * * *